United States Patent
Takata

(10) Patent No.: US 6,558,652 B2
(45) Date of Patent: May 6, 2003

(54) PROCESS FOR PRODUCING GLUCOMANNAN GEL PARTICLES

(75) Inventor: Tadahiko Takata, Hiroshima-ken (JP)

(73) Assignee: Shimizu Chemical Corporation, Mihara (JP)

( * ) Notice: Subject to any disclaimer, the term of this patent is extended or adjusted under 35 U.S.C. 154(b) by 0 days.

(21) Appl. No.: 09/940,521

(22) Filed: Aug. 29, 2001

(65) Prior Publication Data

US 2003/0060518 A1 Mar. 27, 2003

(51) Int. Cl.[7] .......................... A61K 7/075; A61K 7/16; A61K 7/50; C08H 3/05
(52) U.S. Cl. .......................... 424/49; 424/56; 510/121; 510/135; 514/844; 514/944; 516/107; 536/114; 536/123.1
(58) Field of Search ................................ 516/105, 107; 536/114, 123.1; 510/121, 135; 514/944, 844; 424/49, 56

(56) References Cited

U.S. PATENT DOCUMENTS

| | | | | |
|---|---|---|---|---|
| 3,928,322 A | * | 12/1975 | Sugiyama et al. | |
| 4,226,736 A | * | 10/1980 | Bush et al. | 516/107 X |
| 4,330,438 A | * | 5/1982 | Dierassi et al. | |
| 4,505,826 A | * | 3/1985 | Horton | 516/107 X |
| 4,676,976 A | * | 6/1987 | Toba et al. | 516/107 X |
| 4,746,528 A | * | 5/1988 | Prest et al. | 516/107 X |
| 4,882,426 A | * | 11/1989 | Motozato | 536/114 |
| 5,707,972 A | * | 1/1998 | Shimizu | 536/114 X |
| 6,033,651 A | * | 3/2000 | Dolak et al. | 514/944 X |
| 6,126,954 A | * | 10/2000 | Tsaur | 510/121 X |
| 6,225,462 B1 | * | 5/2001 | Berry et al. | 536/123.1 |
| 6,258,342 B1 | * | 7/2001 | Harcum et al. | 424/49 |

\* cited by examiner

*Primary Examiner*—Richard D. Lovering
(74) *Attorney, Agent, or Firm*—Millen, White, Zelano & Branigan, P.C.

(57) ABSTRACT

A particulate glucomannan gel is produced by swelling a glucomannan-rich flour with water in the presence of ethanol, treating the swollen particles with an alkali to form gelled particles followed by drying. The dried gel particles are incorporated into hygenic or cosmetic preparations as a deposit-cleaning agent.

19 Claims, No Drawings

PROCESS FOR PRODUCING GLUCOMANNAN GEL PARTICLES

BACKGROUND OF THE INVENTION

This invention relates to a process for producing glucomannan gel particles which are useful as a deposit-cleaning agent to be formulated into hygenic and cosmetic preparations.

As is well-known, dental pastes generally contain a particulate material such as calcium carbonate, calcium phosphate, calcium sulfate, aluminum hydroxide or silica for removing deposit from the tooth by a scrubbing or exfoliating effect. In order to minimize damages to the enamel and gingiva, synthetic polymer beads have also been used. A particulate material is also used in cosmetic preparations. JP-A-06033416 discloses a skin-cleansing preparation containing a cross-linked polymer bead having a certain degree of elasticity.

The known scrubbing or exfoliating agents are comprised of a particulate material having a uniform physical property throughout the entire sections. It would be desirable to have a particulate material having a dual structure comprising a relatively hard core surrounded by a relatively soft shell layer in order to minimize damages to the tissue to be cleaned while retaining a sufficient scrubbing or exfoliating effect.

SUMMARY OF THE INVENTION

The above need may be met by the present invention. According to this invention, there is provided a process for producing a particulate glucomannan gel comprising:

adding a glucomannan-rich flour in an aqueous ethanol containing about 40 to 50% of ethanol;

allowing the flour particles to swell in the aqueous ethanol;

treating the swollen flour particles with an alkali to form gelled flour particles;

separating the gelled flour particles from the liquid; and drying the gelled flour particles.

The particulate glucomannan gel produced by the above process is particularly suitable for use in hygenic and cosmetic preparations as a deposit-scrubbing or exfoliating agent. The dried gel particles can absorb only a limited amount of water to form a dual structure in which a shell of water-swollen gel surrounds a core of the dried gel. This property is particularly advantageous over the known particulate materials because damages to the tissue to be cleaned are minimized while retaining the scrubbing or exfoliating effect of the particulate material.

Another advantage over the known particulate materials is their massage effect on the skin. The dry gel particles swell to a spherical shape having an adequate size and hardness for rolling on the skin to give the massage effect when absorbing water. At the same time, the rolling gel particles remove, fatty secretional products from the skin. This gives a pleasant feeling to the user.

DETAILED DISCUSSION

Glucomannan is a polysaccharide complex found in the tuber of Amorphophallus species such as *A. Konjac*. Aqueous solutions of glucomannan in the form of a hydrosol produce a water-insoluble, thermally irreversible hydrogel when reacting the sol with an alkali. This process has long been utilized in Japan, China and other countries for the production of a foodstuff called "konjac" from Amorphophallus tuber flour called "konjac flour".

Any glucomannan-rich flour derived from tubers of an Amorphophallus species, typically *A. konjac* may be employed. Purified glucomannan flour and refined konjac flour are preferred. Crude glucomannan-containing flour commonly referred to as "Konjac flour" is a product obtained by slicing, drying and grinding whole tubers of an Amorphophallus species, typically *A. konjac* to a particle size of 0.5 mm or less. Refined konjac flour is produced by pneumatically classifying the crude konjac flour to remove starch or other impurities and has a carbohydrate content of about 80% or higher by weight. Purified glucomannans are produced from crude or refined konjac flour either by washing with water or by precipitating with ethanol to increase the glucomannan content to greater than 90% or higher.

Rapidly dissolvable Konjac flour is produced by grinding the refined konjac flour into finer particles either in the presence of ethanol or in a frozen state. All of these products are commercially available.

The term "glucomannan-rich flour" as-used herein collectively refers to refined konjac flour, purified glucomannan flour and rapidly dissolvable konjac flour.

According to the present invention, the starting glucomannan-rich flour is added to a mixture of water/ethanol containing 40 to 50% of ethanol. Since glucomannan is not soluble in ethanol, the flour particles swell with water in the mixture without dissolving in the mixture.

According to the present invention, the glucomannan-rich flour is allowed to react with an alkali added to the water-ethanol mixture in the swollen state thereby to give discrete particles of irreversible glucomannan hydrogel. The alkali addition may be performed by initially dissolving an amount of alkali in the water-ethanol mixture or adding a solution of alkali following the addition of glucomannan-rich flour to the water-ethanol mixture.

Any alkali such as sodium hydroxide, sodium carbonate, potassium hydroxide or potassium carbonate may be used. A saturated lime water may be preferably used as is common practice in the production of edible konjac. The resulting hydrogel particles are separated from the liquid medium by the conventional method such as centrifugation and then washed well to remove excessive alkali. If necessary, the excessive alkali may be neutralized with a nontoxic organic acid such as acetic or citric acid.

The hydrogel particles are then dried in a drying apparatus preferably at a temperature of about 105° C. Once the hydrogel particles have been dried, they do not fully revert to the original hydrogel particles in water but the dried hard gel particles can absorb an amount of water to form semi-swollen gel particles having a particle size comparable to the particle size of the starting glucomannan-rich flour. The semi-swollen particle comprises a relatively soft shell portion and a relatively hard core portion. It is for this reason that the glucomannan particles of the present invention have no or little damaging effect on the tooth or skin while retaining a sufficient deposit-removing effect when formulating in hygenic or cosmetic preparations including toothpaste and skin-cleansing preparations.

EXAMPLES

The following examples are intended to further illustrate the present invention without limiting thereto. All parts and percents therein are by weight unless otherwise indicated.

Example 1

One kg of commercial refined konjac flour was suspended in a mixture of 8 L of 50% aqueous ethanol and 1 L of a saturated lime solution. The resulting suspension was stirred at room temperature for 2 hours and then contrifuged. The resulting wet cake was resuspended in 5 L of 50% aqueous ethanol. After stirring about 30 minutes, the suspension was centrifuged again to obtain a wet cake. This washing process was repeated several times until the washing solution is substantially free of alkaline substances. If desired, the alkaline substance may be neutralized with a nontoxic organic acid added to the washing solution except the final washing step. The resulting washed wet cake was then dried in a drying apparatus at about 105° C. to obtain dried or anhydrous glucomannan gel particles.

Example 2

This example illustrates typical hygenic and cosmetic formulations containing the gel particles produced in Example 1.

| Material | Parts by weight |
|---|---|
| 1. Cleansing foam | |
| Detergent | 40.0 |
| Emolient | 5.0 |
| Preservative | 0.3 |
| Moisturizer | 15.0 |
| Glucomannan gel particles | 2.0 |
| Perfume | 0.1 |
| Purified water | q.s. |
| Total | 100.0 |
| 2. Toothpaste | |
| Calcium carbonate (heavy) | 40.00 |
| Glycerine | 17.35 |
| CMC sodium | 1.75 |
| Saccharin sodium | 0.20 |
| Butyl p-hydroxybenzoate | 0.20 |
| Sodium laurylsulfate | 2.00 |
| Glucomannan gel particles | 2.00 |
| Lauroylsarcosine sodium | 2.00 |
| Perfume | 1.15 |
| Purified water | q.s. |
| Total | 100.00 |
| 3. Cleansing powder | |
| Glucomannan gel particles | 2.0 |
| Cinnamon extract | 1.5 |
| Aluminum chloride hydroxide | 3.0 |
| 1-Menthol | 0.05 |
| Kaolin | 20.0 |
| Lactose | 0.5 |
| CMC sodium | 0.1 |
| Butyl p-hydroxybenzoate | 0.1 |
| Perfume | q.s. |
| Talc | q.s. |
| Total | 100.0 |
| 4. Face cleansing liquid preparation | |
| Glucomannan gel particles | 3.0 |
| Stearic acid | 5.0 |
| Myristic acid | 12.0 |
| Lauric acid | 7.0 |
| Glycerine fatty acid monoester | 3.0 |
| Sodium acetylglutamate | 20.0 |
| Anhydrous caffeine | 0.03 |
| Glycerine | 10.0 |
| CMC sodium | 0.1 |
| Perfume | q.s. |
| Purified water | q.s. |
| Total | 100.0 |
| 5. Shampoo | |
| Glucomannan gel particles | 5.0 |
| Cocunut fatty acid diethanolamide | 5.0 |
| Sodium polyoxyethylenelauryl sulfate | 15.0 |
| Sodium polyoxyethylenealkyl-sulfosuccinate | 7.0 |
| Coconut fatty acid propyldimethyl-aminoacetic betaine | 10.0 |
| Anhydrous caffeine | 0.1 |
| CMC sodium | 0.2 |
| Perfume | q.s. |
| Purified water | q.s. |
| Total | 100.0 |
| 6. Rinser liquid | |
| Glucomannan gel particles | 2.0 |
| Stearyl trimethylammonium chloride | 2.0 |
| Cetyl alcohol | 2.0 |
| Silicone oil | 3.0 |
| Polyoxyethylene(10)oleyl ether | 1.0 |
| Glycerine | 5.0 |
| Polyethyleneglycol | 0.05 |
| Butyl p-hydroxybenzoate | 0.05 |
| Perfume | q.s. |
| Purified water | q.s. |
| Total | 100.0 |

I claim:

1. A process for preparing a particulate glucomannan gel comprising:
   adding a glucomannan-rich flour to an aqueous ethanol containing about 40 to 50% of ethanol;
   allowing the flour particles to swell in the aqueous ethanol;
   treating the swollen flour particles with an alkali to form gelled flour particles;
   separating the gelled flour particles from the liquid; and
   drying the gelled flour particles.

2. A process according to claim 1, wherein the alkali is sodium hydroxide, sodium carbonate, potassium hydroxide or potassium carbonate.

3. A process according to claim 1 further comprising after separating the gelled flour particles from the liquid the washing of the gelled flour particles to remove alkali and/or neutralizing the alkali with a nontoxic organic acid.

4. A process according to claim 1, wherein the gelled flour particles are dried at a temperature of about 105° C.

5. A process according to claim 1 wherein said glucomannan-rich flour has a glucomannan content of at least about 80%.

6. A particulate glucomannan gel produced by the process of claim 5.

7. A hygienic or cosmetic composition comprising a deposit-cleaning amount of the particulate glucomannan gel of claim 6 and a hygienically or cosmetically acceptable carrier.

8. A process according to claim 1 wherein said glucomannan-rich flour is refined konjac flour or purified glucomannan flour.

9. A particulate glucomannan gel produced by the process of claim 8.

10. A hygienic or cosmetic composition comprising a deposit-cleaning amount of the particulate glucomannan gel of claim 9 and a hygienically or cosmetically acceptable carrier.

11. A process according to claim 1 wherein said alkali is a saturated lime solution.

12. A particulate glucomannan gel produced by the process of claim 11.

13. A hygienic or cosmetic composition comprising a deposit-cleaning amount of the particulate glucomannan gel of claim 12 and a hygienically or cosmetically acceptable carrier.

14. A particulate glucomannan gel produced by the process of claim 1.

15. A hygienic or cosmetic composition comprising a deposit-cleaning amount of the particulate glucomannan gel of claim 14 and a hygienically or cosmetically acceptable carrier.

16. A cleasing foam, a toothpaste, a cleansing powder, a face cleansing liquid composition, a shampoo, or a rinser liquid comprising a deposit-cleaning amount of the particulate glucomannan gel of claim 14.

17. A deposit-cleaning particulate material consisting essentially of dried, alkali-gelled water-insoluble glucomannan rich flour particles which absorb an amount of water not sufficient to completely swell said dried particles to form a shell of water-swollen hydrogel surrounding a core of the dried gel.

18. A hygienic or cosmetic composition comprising a deposit-cleaning particulate material of claim 17.

19. A cleansing foam, a toothpaste, a cleansing powder, a face cleansing liquid composition, a shampoo, or a rinser liquid comprising a deposit-cleaning particulate material of claim 17.

* * * * *

UNITED STATES PATENT AND TRADEMARK OFFICE
CERTIFICATE OF CORRECTION

PATENT NO. : 6,558,652 B2
DATED : May 6, 2003
INVENTOR(S) : Tadahiko Takata

It is certified that error appears in the above-identified patent and that said Letters Patent is hereby corrected as shown below:

<u>Title page,</u>
Item [73], Assignee, reads "Mihara," should read -- Hiroshima --

<u>Column 6,</u>
Line 1, reads "cleasing," should read -- cleansing --

Signed and Sealed this

Nineteenth Day of October, 2004

JON W. DUDAS
*Director of the United States Patent and Trademark Office*